United States Patent [19]
Asano et al.

[11] Patent Number: 5,908,437
[45] Date of Patent: Jun. 1, 1999

[54] REMOTELY ACTUATED SURGICAL INSTRUMENT

[75] Inventors: Tamoru Asano, Gifu; Makoto Mori, Kakamigahara, both of Japan

[73] Assignee: Kai R&D Center Co., Ltd., Gifu, Japan

[21] Appl. No.: 08/957,382

[22] Filed: Oct. 24, 1997

[30] Foreign Application Priority Data

Nov. 1, 1996 [JP] Japan ................................. 8-291957
Jun. 12, 1997 [JP] Japan ................................. 9-155110

[51] Int. Cl.$^6$ ................................................. A61B 17/28
[52] U.S. Cl. .................................... 606/205; 606/167
[58] Field of Search ..................... 606/45–52, 205–211, 606/167, 174

[56] References Cited

U.S. PATENT DOCUMENTS

| | | |
|---|---|---|
| 3,895,636 | 7/1975 | Schmidt . |
| 4,815,460 | 3/1989 | Porat et al. . |
| 5,133,727 | 7/1992 | Bales et al. ........................ 606/207 |
| 5,170,800 | 12/1992 | Smith et al. . |
| 5,228,451 | 7/1993 | Bales et al. . |
| 5,417,709 | 5/1995 | Slater .................................. 606/207 |
| 5,419,339 | 5/1995 | Palmer . |
| 5,478,350 | 12/1995 | Kratsch et al. . |
| 5,482,054 | 1/1996 | Slater et al. . |
| 5,507,296 | 4/1996 | Bales et al. . |

Primary Examiner—Glenn K. Dawson
Attorney, Agent, or Firm—Limbach & Limbach L.L.P.

[57] ABSTRACT

A surgical instrument having an insert member for insertion of a treatment device, which is located at a distal end of the insert member into a tissue body. The treatment device is remotely manipulated by an operational wire. The instrument includes a support shaft and treatment members, such as forceps, rotatably supported by the support shaft. Actuating levers extend from the treatment members. Each of the actuating levers has a connection hole. Link wires are located between the operational wire and the actuating levers. Distal ends of the link wires are hooked to the connection holes, and proximal ends of the link wires are connected to the operational wire. The construction of the instrument permits the treatment device to be initially actuated with very little force by the operational wire.

19 Claims, 7 Drawing Sheets

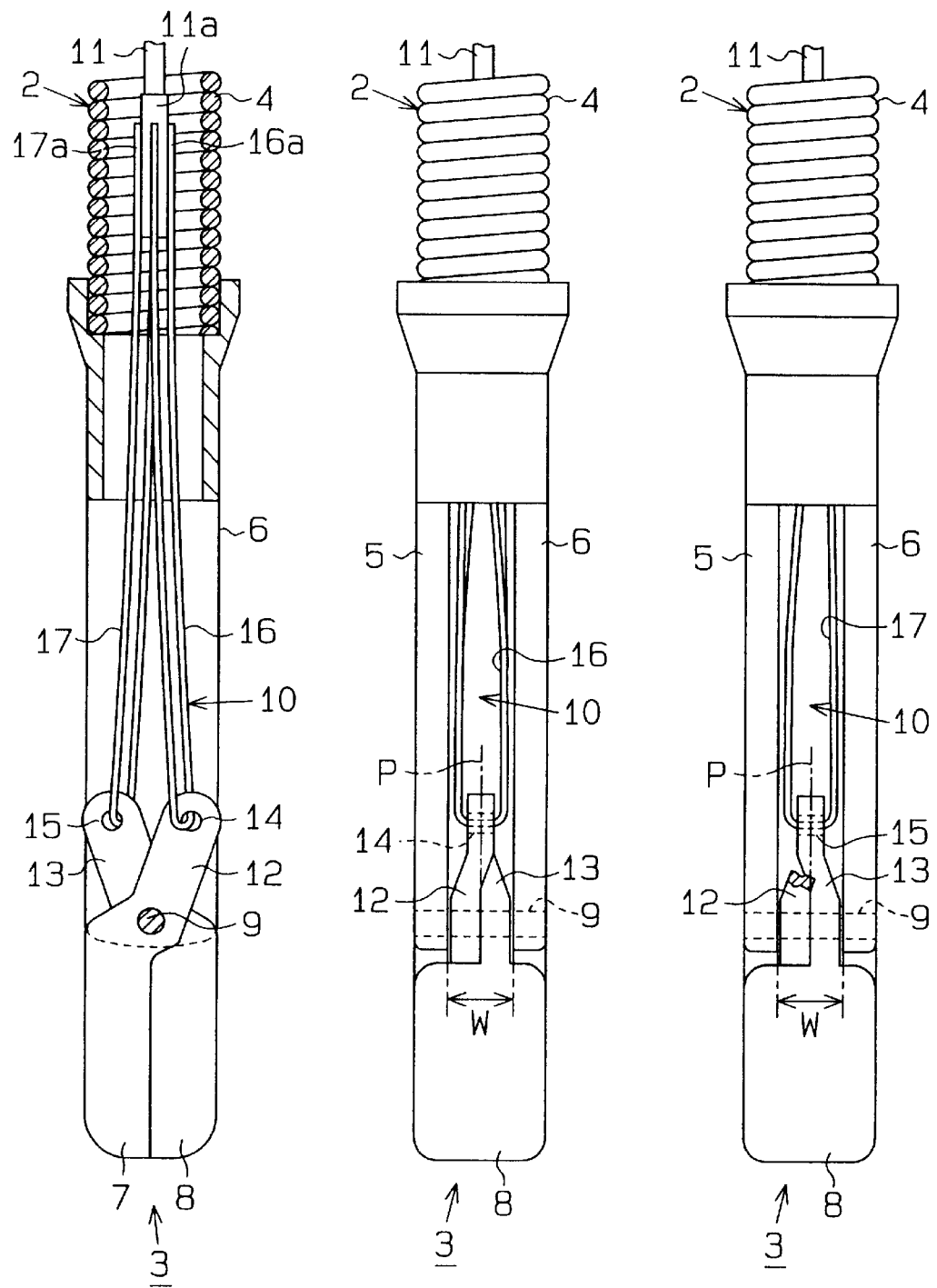

Fig.4(a)
Fig.4(b)
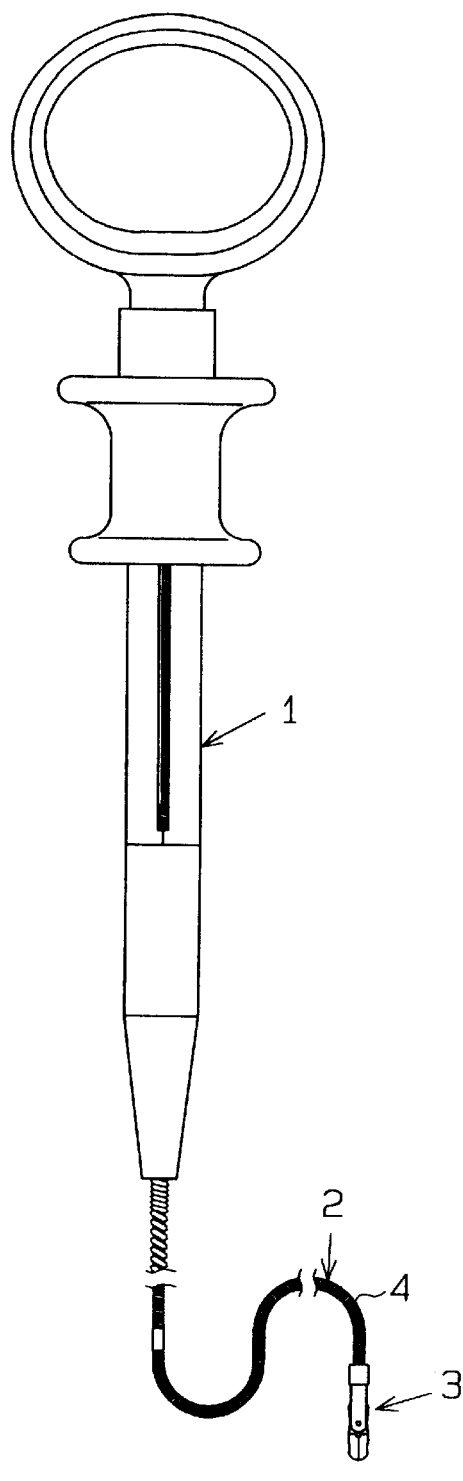
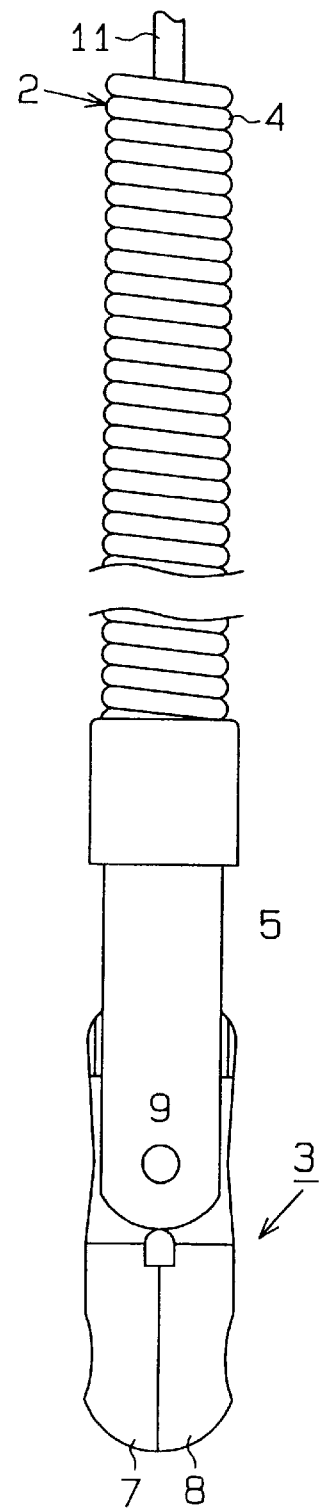

REMOTELY ACTUATED SURGICAL INSTRUMENT

BACKGROUND OF THE INVENTION

The present invention relates to surgical instruments, such as forceps, which are used in surgery and medical procedures. More particularly, the present invention pertains to the structure of a remotely actuated treatment device, which is located at the distal end of an insert member.

FIGS. 7(a) and 7(b) show a typical prior art surgical instrument. The instrument has a pair of cup-shaped cutting jaws 7 and 8 that are rotatably supported by a fixed center shaft 9. The instrument also includes a link mechanism 10 that opens and closes the jaws 7, 8. The link mechanism 10 is remotely manipulated by an operational wire 11. The closing motion of the jaws 7, 8 removes body tissue when the device is appropriately positioned within a human or animal body.

The link mechanism 10 includes actuating levers 12, 13 extending from the jaws 7, 8, respectively. Actuating links 26 and 27 are rotatably coupled to the levers 12, 13 by actuating shafts 28, 29. The links 26 and 27 are rotatably supported on the distal end 11a of the operational wire 11 by a movable center shaft 30.

The link mechanism 10 includes the actuating levers 12, 13, or rigid links, and the actuating links 26, 27. The levers 12, 13 and the links 26, 27 are pivotally coupled by the fixed shaft 9, the actuating shafts 28, 29 and the movable shaft 30. When assembling the mechanism 10, the holes in the links 26, 27 have to be aligned with the holes in the levers 12, 13 and with the hole in the distal end 11a of the operational wire 11 such that the shafts 28, 29 and 30 can be inserted in the aligned holes. The assembly of the mechanism 10 is therefore troublesome.

SUMMARY OF THE INVENTION

Accordingly, one of the objectives of the present invention is to construct a surgical instrument that is easier to assemble than prior art models.

Another objective of the present invention is to construct a surgical instrument that is easily actuated with only a minimum force, particularly at the initial stage of actuation.

To achieve the foregoing and other objectives and in accordance with the purpose of the present invention, an improved surgical instrument is provided. The surgical instrument has an insert member for insertion of a treatment device, which is located at a distal end of the insert member, into a tissue body. The treatment device is remotely actuated by an operational wire. The instrument includes a support shaft, an actuating lever and a link wire. The treatment device includes a treatment member rotatably supported by the support shaft. The actuating lever is connected to the treatment member. The actuating lever has a coupling hole formed therein. The link wire is located between the operational wire and the actuating lever. The link wire has a distal end and a proximal end. The distal end of the link wire is hooked to the coupling hole and the proximal end of the link wire is connected to the operational wire.

Other aspects and advantages of the invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which:

FIG. 3(a) is a front cross-sectional view of the instrument of FIG. 1(b);

FIG. 3(b) is a right side view illustrating the instrument of FIG. 1(b);

FIG. 3(c) is a right side view, with some parts cut away, illustrating the instrument of FIG. 1(b);

FIG. 4(a) is a front view, with some sections removed, illustrating a surgical instrument of a further embodiment according to the present invention;

FIG. 4(b) is an enlarged partial front view illustrating a distal end of the surgical instrument of FIG. 4(a) when the jaws are closed;

DETAILED DESCRIPTION OF THE PREFERRED EMBODIMENTS

Figure 1:
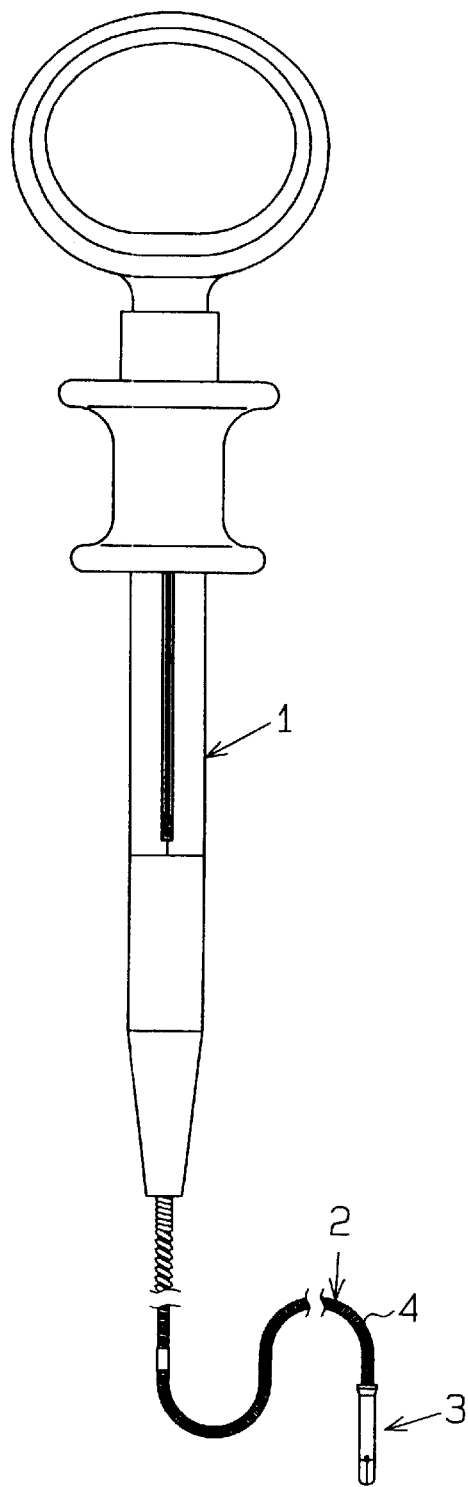
FIG. 1(a) is a front view, with some sections removed, illustrating a surgical instrument of a first embodiment according to the present invention.
FIG. 1(b) is an enlarged partial front view illustrating a distal end of the surgical instrument of FIG. 1(a) when the jaws are closed.
Figure 1:
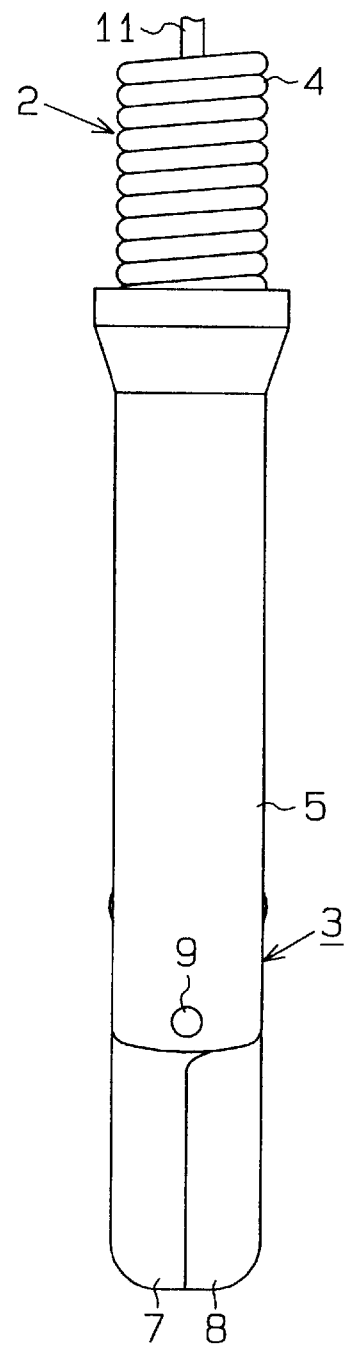

A first embodiment of the present invention will now be described with reference to FIGS. 1 to 3.

Referring to FIG. 1(a), an insert member 2, which extends from a manipulator 1, is inserted into a tissue body while being monitored by an endoscope (not shown). A treatment device 3 is connected to the distal end of the insert member 2.

As shown in FIGS. 1(b), 2(a), 3(a), 3(b) and 3(c), a coil 4 is wound around an operational wire to form the outer surface of the insert member 2. Housing plates 5 and 6 are attached to the distal end of the coil 4. A pair of cup like cutting jaws 7 and 8 (a first treatment member and second treatment member) are rotatably supported by the housings 5, 6 with a fixed support shaft 9. The jaws 7 and 8 are opened and closed by a link mechanism 10 for removing tissue. The link mechanism 10 is remotely manipulated from the manipulator 1 by the operational wire 11 located in the insert member 2. The jaws 7, 8 are formed by metal injection molding. The jaws 7, 8 may alternatively be formed by machining metal stock.

The link mechanism 10 includes a first actuating lever 12, which integrally extends from the first jaw 7, and a second actuating lever 13, which integrally extends from the second jaw 8. Connection holes 14, 15 are formed in the free ends of the levers 12 and 13, respectively. Link wires 16, 17 are passed through and are hooked in the holes 14, 15. The proximal ends 16a, 17a of the wires 16, 17 are fastened to the periphery of the operational wire 11 by, for example, spot welding. Like a piano wire, the wires 16, 17 have a predetermined rigidity, plasticity and elasticity.

As shown in FIGS. 3(b) and 3(c), the proximal ends of the first and second actuating levers 12, 13 overlap each other. The middle portions of the levers 12 and 13 are bent inward toward the central axis P of the instrument. The free ends of the levers 12 and 13 are aligned with the axis P.

Figure 2A:
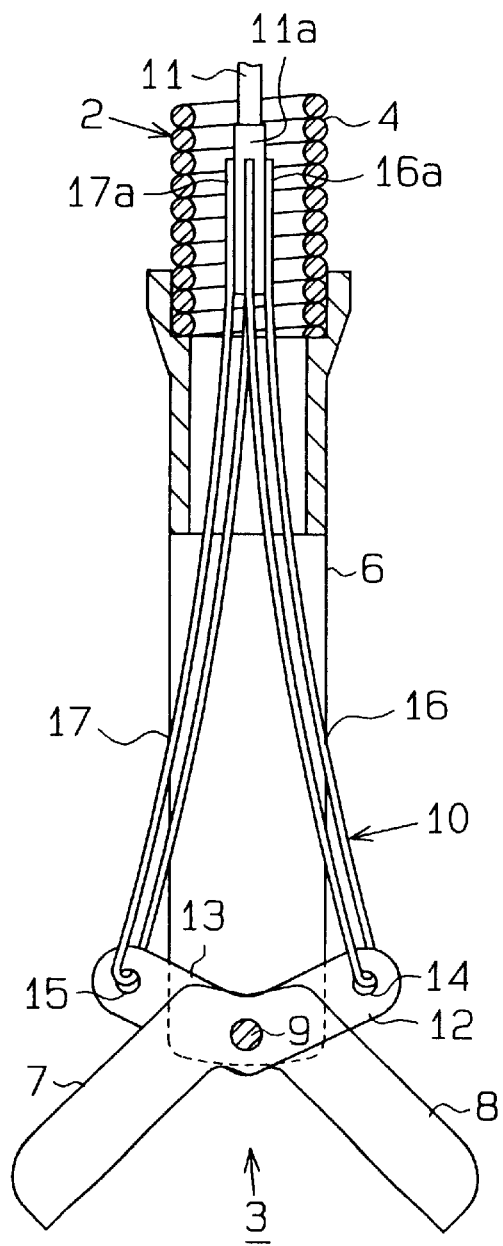
FIG. 2(a) is an enlarged partial cross-sectional view illustrating the surgical instrument of FIG. 1(b) when the cutting jaws are open.

The wire 11 is pulled remotely by the manipulator 1. This causes the link wires 16, 17 to rotate the first and second actuating levers 12, 13 toward each other as illustrated in FIGS. 2(a) and 3(a). The first and second jaws 7, 8 are closed, or engaged with each other, accordingly. When the manipulator 1 pushes the wire 11, the first and second actuating levers 12, 13 are rotated away from each other. This opens, or separates, the first and second jaws 7, 8 as illustrated in FIG. 2(a).

The first embodiment has the following advantages.

The link wires 16, 17 are coupled to the levers 12, 13 simply by threading the wires 16, 17 through the holes 14, 15 of the levers 12, 13. This simplifies the coupling of the levers 12, 13 and the wires 16, 17.

The link wires 16, 17 are secured to the operational wire 11 simply by welding their ends 16a, 17a to the periphery of the distal end 11a of the wire 11. This simplifies the fastening of the link wires 16, 17 to the operational wire 11.

Figure 2B:
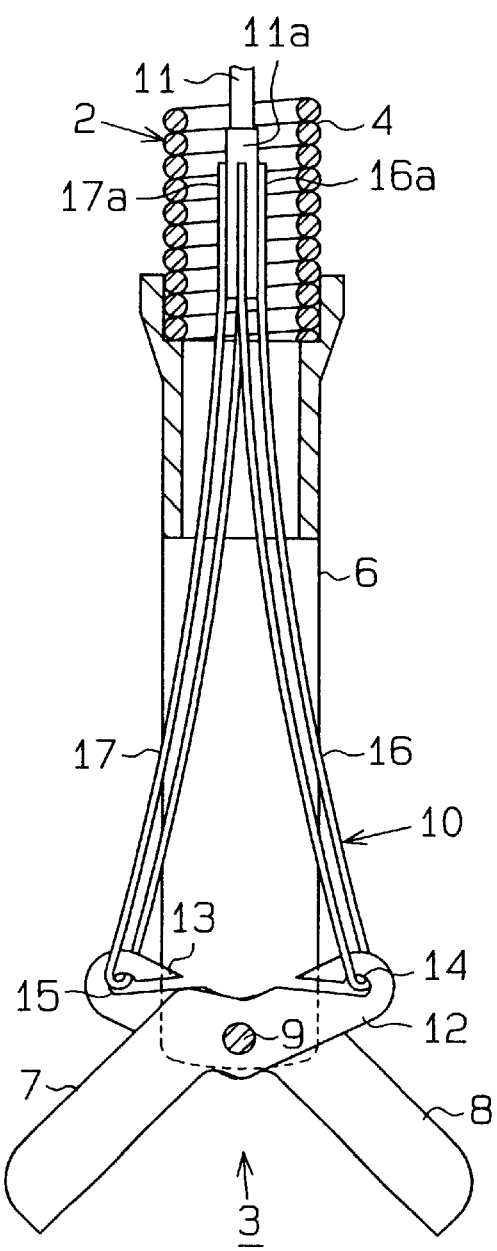
FIG. 2(b) is a view like FIG. 2(a) illustrating a surgical instrument of a further embodiment.

As illustrated in FIG. 2(b), slots may be formed in the actuating levers 12, 13 such that the holes 14, 15 open to the periphery of the levers 12, 13.

In the treatment device 3 of the first embodiment, the cup like jaws 7 and 8 are supported by the fixed support shaft 9 to rotate relative to each other. However, the shape of the jaws is not limited to a cup like shape. Further, the number of the jaws, or the number of the treatment members, may be less than or more than two. For example, a treatment member may be rotatably supported on the instrument, and a single link wire may be coupled to the treatment member so that the link wire causes the treatment member to pivot.

A hole (not shown) may be formed in the distal end 11a of the operational wire 11. In this case, the distal end 11a is flattened or otherwise deformed after passing the link wires 16, 17 through the hole such that the link wires 16, 17 are fixed to the operational wire 11.

A surgical instrument according to a further embodiment of the present invention will now be described with reference to FIGS. 4 to 6. The differences from the first embodiment will mainly be discussed below, and like or the same reference numerals are given to those components that are like or the same as the corresponding components of the first embodiment.

Figure 5A:
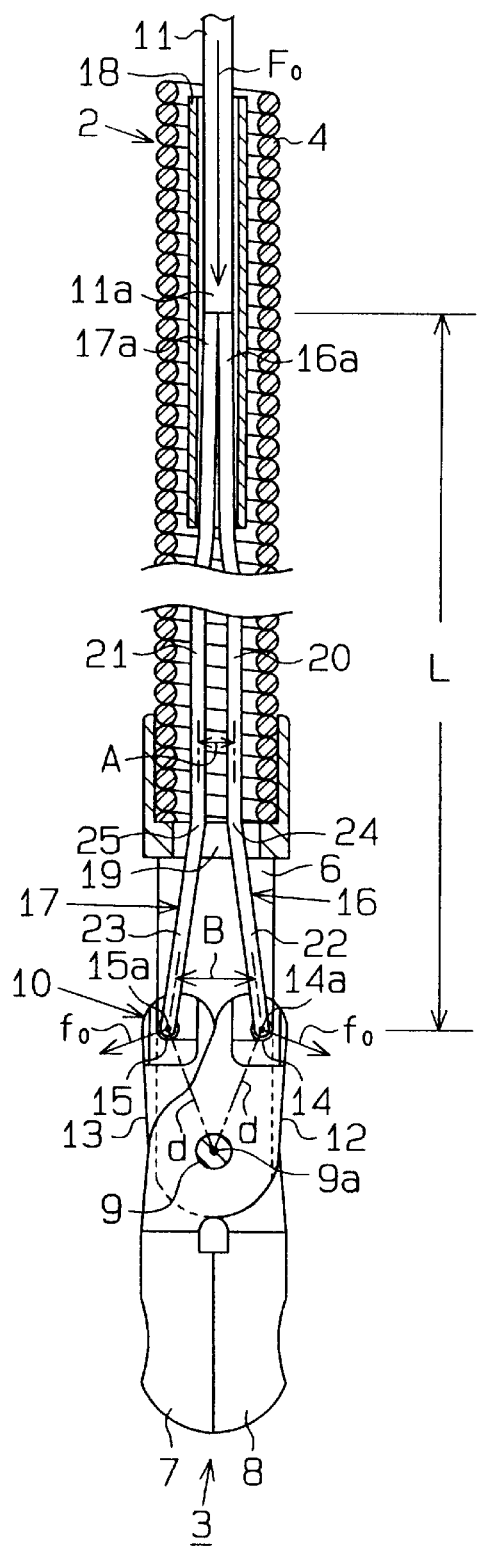
FIG. 5(a) is a partial front cross-sectional view illustrating the instrument of FIG. 4(b)
Figure 5B:
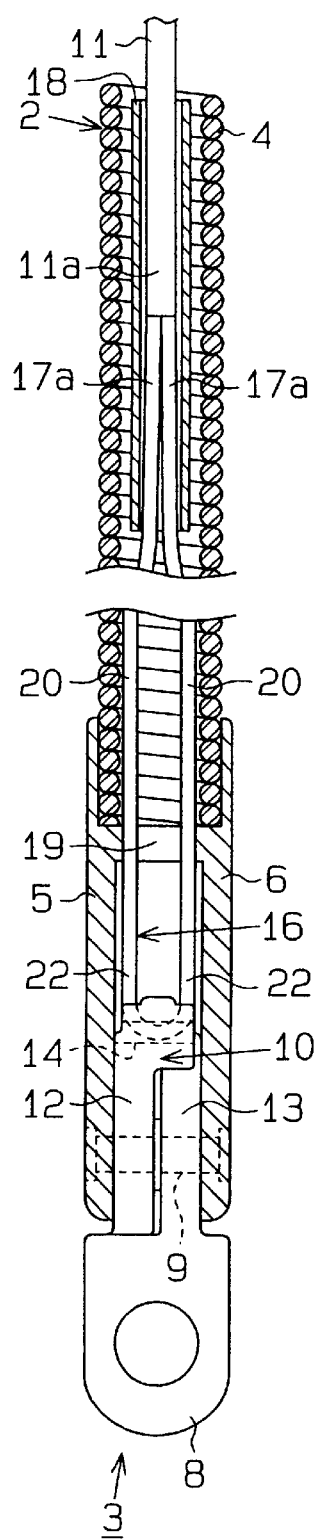
FIG. 5(b) is a partial right side cross-sectional view illustrating the instrument of FIG. 4(b)

As shown in FIGS. 5(a) and 5(b), the ends 16a, 17a of the link wires 16, 17 are welded to the operational wire 11 with the end faces of the wires 16, 17 contacting the end face of the wire 11. The welded part is covered by a tube 18. Thus, as in the first embodiment, coupling of the link wires 16, 17 and the operational wire 11 is facilitated.

The length L of the link wires 16, 17 is set longer than 10 mm and is preferably 100 to 400 mm. The longer the distance L is, the more flexible the insert member 2 is adjacent to the treatment device 3.

The link wires 16, 17 pass through a narrow opening 19 formed at the distal end of the coil 4 and are coupled to the actuating levers 12, 13, which are separated by a distance that is greater than the size of the opening 19. The link wires 16, 17 include proximal portions 20, 21, which are accommodated in the insert member 2, and distal portions 22, 23, which are located outside the insert member 2. The boundaries of the proximal portions 20, 21 and the distal portions 22, 23 are bent at obtuse angles to form angles 24, 25. The distance A between the proximal portions 20 and 21 is smaller than the distance B between the distal portions 22 and 23.

FIGS. 5(a) and 5(b) show a state where the jaws 7, 8 are closed. As described above, the angles 24, 25 are formed in the link wires 16, 17. Thus, the distal portions 22 and 23 are not held apart against the resilient force of the link wires 16, 17 when the jaws 7 and 8 are closed. In other words, the link wires 16, 17 are substantially relaxed when the jaws 7, 8 are closed.

When the jaws 7, 8 are closed, the angles 24, 25 generate little resilient restoring force acting on the distal portions 22, 23. Therefore, the force of the link wires 16 and 17 in a direction closing the first and second jaws 7 and 8 is substantially zero.

The process of moving of the jaws 7 and 8 illustrated in FIGS. 5(a) and 5(b) to the open state illustrated in FIG. 6 will now be described. When the jaws 7, 8 are closed as shown in FIGS. 5(a), 5(b), the operational wire 11 is remotely pushed by the manipulator 1 with an initial actuating force $F_0$. This applies an initial rotating force $f_0$, which is a component of the force $F_0$, to each of the actuating levers 12 and 13. If the distances between the rotational axis 9a of the support shaft 9 and the rotational axes 14a, 15a of the link wires 16, 17 in the holes 14, 15 are the same (distance d), the initial rotating moment $M_0$ is expressed by the following equation.

$$M_0 = f_0 \times d$$

The initial rotating moment $M_0$ gradually opens the actuating levers 12, 13. Accordingly, the distances A and B between the link wires 16 and 17 are gradually widened from the angles 24, 25 to the distal portions 22, 23. This flexes the distal portions 22, 23 against the resilient forces of the distal portions 22, 23. The resilient forces of the distal portions 22, 23 function as component forces that close the levers 12, 13. If the initial moment of resistance acting on the levers 12, 13 is represented by $N_0$, the resultant actuating moment T (not shown) generated by the initial actuating force $F_0$ is expressed by the following equation.

$$T = M_0 - N_0$$

As the levers 12, 13 are spread further, the resilient forces of the distal portions 22, 23 increase. The resistance moment N increases, accordingly. On the other hand, the rotational forces f acting on the levers 12, 13 are also increased as the levers 12, 13 are spread further and the rotating moment M increases, accordingly.

Generally, the resultant actuating moment T generated by the initial actuating force $F_0$ varies in accordance with the difference between the rotating moment M and the resistance moment N. Thus, changing the actuating force F from the initial actuating force $F_0$, as necessary, smoothly opens the levers 12 and 13.

The relationship between the rotating moment M and the resistance moment N varies in accordance with the magnitude of the actuating force F. That is, changing the magnitude of the force F causes the rotating moment M to be greater than the resistance moment N (M>N), equal to the resistance moment N (M=N) or smaller than the resistance moment N (M<N). In any case, properly changing the magnitude of the force F smoothly opens the levers 12, 13

Figure 6:
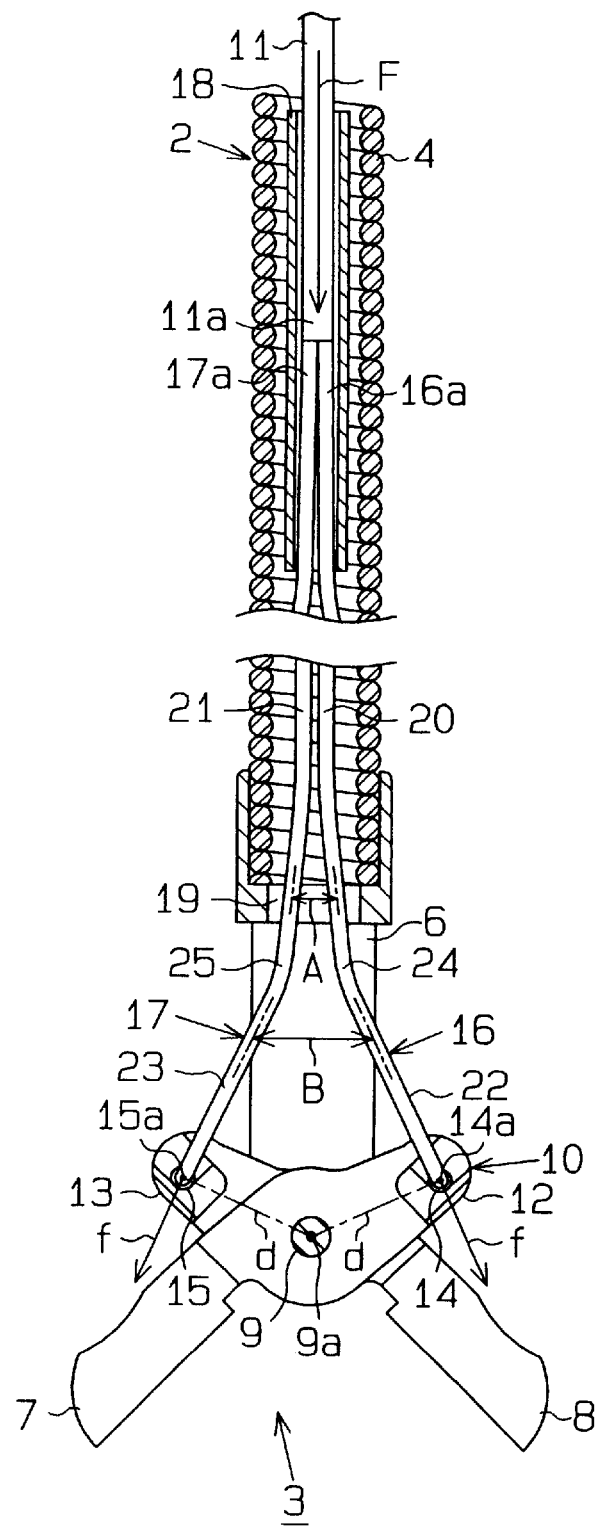
FIG. 6 is an enlarged partial front cross-sectional view illustrating the instrument of FIG. 4(b) when the cutting jaws are open.
Figure 7A:
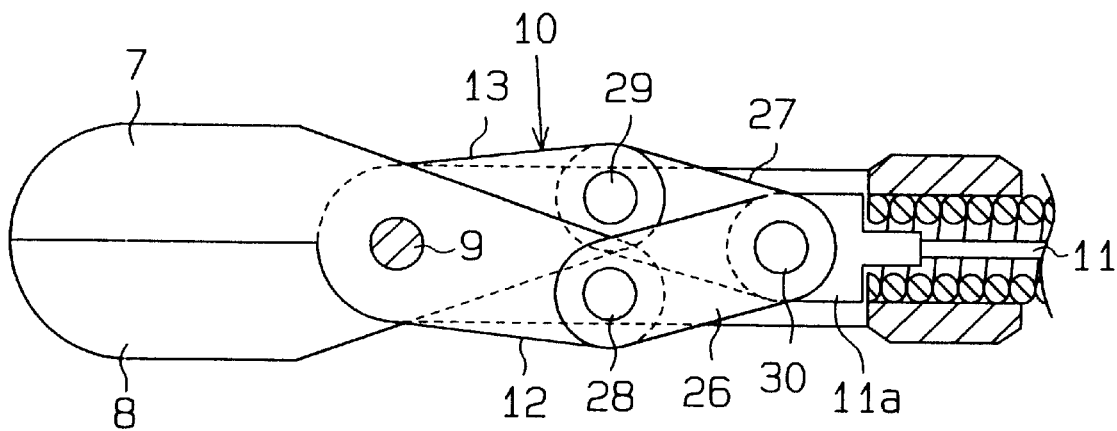
FIG. 7(a) is an enlarged partial cross-sectional view illustrating a prior art surgical instrument when cutting jaws are closed.
Figure 7B:
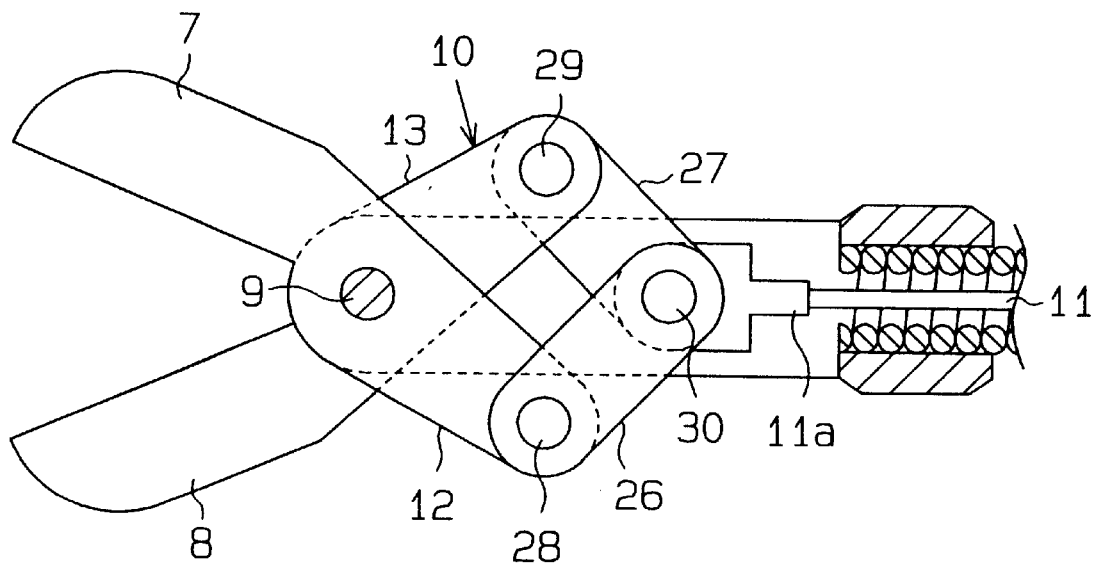
FIG. 7(b) is an enlarged partial cross-sectional view illustrating the surgical instrument of FIG. 7(a) when the cutting jaws are open.

FIG. 6 shows a state where the jaws 7 and 8 are open. Even in this state, the equation ($T=M_0-N_0$) is satisfied.

The process of moving the jaws 7, 8 move from the state of FIG. 6 to the state of FIG. 5 will now be described. The operational wire 11 is pulled by the manipulator 1 with an actuating force (−F). The resultant returning moment (−T) generated by the force (−F) is the sum of the returning moment (−M) and the resistance moment (−N). The levers 12, 13 are thus smoothly closed.

As described above, the equation ($T=M_0-N_0$) is satisfied in the second embodiment. Therefore, when the jaws 7, 8 are closed as shown in FIG. 5(*a*), the distal portions 22, 23 of the link wires 16, 17 have little resilient restoring force, and the force pushing the jaws 7 and 8 against each other is thus substantially zero. The initial resistance moment $N_0$ is substantially zero, accordingly. This equalizes the resultant actuating moment T with the initial rotating moment $M_0$, thereby minimizing the magnitude of the initial actuating force $F_0$ required for generating the actuating moment T. Thus, when opening the jaws 7, 8 from the closed state, the jaws 7, 8 are actuated with a minimal force $F_0$.

It should be apparent to those skilled in the art that the present invention may be embodied in many other specific forms without departing from the spirit or scope of the invention. Particularly, it should be understood that the invention may be embodied in the following forms.

Therefore, the present examples and embodiments are to be considered as illustrative and not restrictive and the invention is not to be limited to the details given herein, but may be modified within the scope and equivalence of the appended claims.

What is claimed is:

1. A surgical instrument having an insert member for insertion of a treatment device, which is located at a distal end of the insert member, into a tissue body, wherein the treatment device is remotely actuated by an operational wire, the instrument comprising:

a support shaft, wherein the treatment device includes a treatment member rotatably supported by the support shaft;

an actuating lever connected to the treatment member, the actuating lever having a coupling hole formed therein; and a link wire located between the operational wire and the actuating lever, wherein the link wire is formed by folding a single wire to form a folded end and a pair of free ends, the link wire being threaded through the coupling hole at the folded end and the free ends being fixed to the operational wire, the folded end of the link wire being hooked to the coupling hole and the free ends of the link wire being connected to the operational wire.

2. The surgical instrument according to claim 1, wherein:

the treatment member is a first treatment member, and wherein the treatment device includes a second treatment member cooperating with the first treatment member;

the actuating lever is a first actuating lever, and wherein the instrument includes a second actuating lever connected to the second treatment member; and the link wire is a first link wire and wherein the instrument includes a second link wire located between the operational wire and the second actuating lever, wherein a distal end of the second link wire is hooked to a coupling hole formed in the second actuating lever in the same manner as the first link wire is coupled to the first actuating lever.

3. The surgical instrument according to claim 2, wherein each treatment member has a cup shape.

4. The surgical instrument according to claim 2, wherein the first and second link wires extend in generally the same direction with a predetermined distance between them, each link wire having a proximal section accommodated in the insert member and a distal section exposed from the insert member, wherein the distance between the distal sections of the first and second link members is greater than that between the proximal sections.

5. The surgical instrument according to claim 4, wherein each link wire is permanently bent to define a predetermined angle between the proximal section and the distal section.

6. The surgical instrument according to claim 2, wherein each link wire is elastic.

7. The surgical instrument according to claim 6, wherein a force acting on the first and second treatment members to close them due to the elasticity of the link wire is substantially zero while the first and second treatment members are closed.

8. The surgical instrument according to claim 2, wherein each actuating lever is formed integrally with the associated treatment member.

9. The surgical instrument according to claim 8, wherein the first and second actuating levers have proximal portions that overlap with each other, middle portions that extend inwardly toward a plane containing a central axis of the surgical instrument, and distal portions that are placed side by side along the central axis.

10. The surgical instrument according to claim 1, wherein each free end of the link wire is welded to the operational wire.

11. A surgical instrument having an insert member for insertion of a treatment device, which is located at a distal end of the insert member, into a tissue body, wherein the treatment device is remotely actuated by an operational wire, the surgical instrument comprising:

a support shaft, wherein the treatment device includes a pair of first and second cutting jaws rotatably supported by the support shaft;

an actuating lever connected to each cutting jaw, the actuating lever having a coupling hole formed therein; and a link wire having elasticity located between the operational wire and each actuating lever, the link wire having a distal end and a proximal end, the distal end of the link wire being hooked to the coupling hole and the proximal end of the link wire being connected to the operational wire;

wherein a force acting on the first and second cutting jaws to close them due to the elasticity of the link wire is set at substantially zero while the first and second cutting jaws are closed.

12. The surgical instrument according to claim 11, wherein each cutting jaw has a cup shape.

13. The surgical instrument according to claim 11, wherein the link wire is formed by folding a single wire midway along its length to form a folded end and a pair of free ends, the single wire being threaded through the coupling hole at the folded end and the free ends being fixed to the operational wire.

14. The surgical instrument according to claim 13, wherein each free end of the link wire is welded to the operational wire.

15. The surgical instrument according to claim 11, wherein the first and second link wires extend in generally the same direction with a predetermined distance between them, each link wire having a proximal section accommodated in the insert member and a distal section exposed from the insert member, wherein the distance between the distal sections of the first and second link members is greater than that between the proximal sections.

16. The surgical instrument according to claim 15, wherein each link wire is permanently bent to define a predetermined angle between the proximal section and the distal section.

17. The surgical instrument according to claim 11, wherein each actuating lever is formed integrally with the associated cutting jaw.

18. The surgical instrument according to claim 11, wherein the first and second actuating levers have proximal portions that overlap with each other, middle portions that extend inwardly toward a plane containing a central axis of the surgical instrument, and distal portions that are placed side by side along the central axis.

19. A surgical instrument comprising:

an elongated insert member;

an operational wire located within the insert member;

a pair of forceps located at a distal end of the insert member, wherein the forceps include a pair of actuating levers, each actuating lever having a pivotal coupling;

a pair of elongated, elastic, flexible link members located between the actuating levers and the operational wire, each link member being a folded wire having a folded end and a pair of free ends, wherein the folded end of each link member is pivotally coupled to a corresponding one of the actuating levers, and the free ends of each link member are immovably fixed to the operational wire.

* * * * *